(12) United States Patent
Camus et al.

(10) Patent No.: US 7,796,796 B2
(45) Date of Patent: Sep. 14, 2010

(54) OPERATING METHOD FOR AN IMAGE-GENERATING MEDICAL ENGINEERING ASSEMBLY AND ARTICLES ASSOCIATED HEREWITH

(75) Inventors: Estelle Camus, Erlangen (DE); Martin Kleen, Furth (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 1077 days.

(21) Appl. No.: 11/498,440

(22) Filed: Aug. 3, 2006

(65) Prior Publication Data

US 2007/0031018 A1 Feb. 8, 2007

(30) Foreign Application Priority Data

Aug. 3, 2005 (DE) .................. 10 2005 036 564

(51) Int. Cl.
*G06K 9/00* (2006.01)
*H05G 1/00* (2006.01)

(52) U.S. Cl. ............... 382/130; 382/154; 378/210; 128/922

(58) Field of Classification Search ......... 382/128–132, 382/154, 209; 378/210; 128/922
See application file for complete search history.

(56) References Cited

U.S. PATENT DOCUMENTS

| 4,611,340 | A | * | 9/1986 | Okazaki ................. 378/95 |
| 4,794,450 | A | * | 12/1988 | Saito et al. ............... 348/61 |
| 5,319,696 | A | * | 6/1994 | Abdel-Malek et al. ...... 378/108 |
| 5,533,085 | A | * | 7/1996 | Sheehan et al. ........... 378/95 |
| 5,636,636 | A | * | 6/1997 | Kuhn et al. ............... 600/415 |
| 6,066,949 | A | * | 5/2000 | Alley et al. ............... 324/309 |
| 6,151,405 | A | * | 11/2000 | Douglass et al. ........... 382/133 |
| 6,507,668 | B1 | * | 1/2003 | Park ........................ 382/169 |
| 6,529,757 | B1 | * | 3/2003 | Patel et al. ................ 600/407 |
| 6,574,500 | B2 | * | 6/2003 | Keren ....................... 600/431 |
| 6,687,527 | B1 | * | 2/2004 | Wu et al. ................... 600/410 |
| 6,754,522 | B2 | * | 6/2004 | Keren ....................... 600/431 |
| 6,842,638 | B1 | * | 1/2005 | Suri et al. .................. 600/425 |
| 6,853,857 | B2 | * | 2/2005 | Pfeiffer et al. ............. 600/436 |
| 6,909,436 | B1 | * | 6/2005 | Pianykh et al. ............. 345/619 |
| 6,937,884 | B1 | * | 8/2005 | Barbour .................... 600/473 |

(Continued)

FOREIGN PATENT DOCUMENTS

EP 1 004 891 A2 5/2000

OTHER PUBLICATIONS

Waechter et al "Model Based Blood Flow Quantification from Rotational Angiography" Medical Image Analysis pp. 568-602.*

(Continued)

*Primary Examiner*—Matthew C Bella
*Assistant Examiner*—Mia M Thomas (57) ABSTRACT

A controller of an image-generating medical engineering assembly receives a selection of an image valuation method from a user. It subsequently automatically adjusts selection-specific, positioning-independent operating parameters of the recording arrangement and or provides the user with instructions for adjusting the positioning-independent operating parameters. In response to a user's start input the controller captures by means of a recording arrangement of the image-generating medical engineering assembly a sequence of successive two-dimensional images of an iteratively moving object being examined and capturing instants thereof as well as a phase signal of the object being examined and archives the sequence of images, capturing instants and the phase signal.

18 Claims, 8 Drawing Sheets

U.S. PATENT DOCUMENTS

| | | | | |
|---|---|---|---|---|
| 6,954,767 | B1* | 10/2005 | Kanada | 1/1 |
| 6,978,112 | B2* | 12/2005 | Kaburagi et al. | 399/366 |
| 7,433,504 | B2* | 10/2008 | Deischinger et al. | 382/128 |
| 7,519,414 | B2* | 4/2009 | Mitschke et al. | 600/424 |
| 7,623,622 | B2* | 11/2009 | Camus et al. | 378/62 |
| 7,657,069 | B2* | 2/2010 | Boese et al. | 382/128 |
| 7,668,294 | B2* | 2/2010 | Kargar et al. | 378/98.8 |
| 7,668,361 | B2* | 2/2010 | Spies | 382/132 |
| 2001/0012328 | A1* | 8/2001 | Koppe et al. | 378/62 |
| 2002/0032376 | A1 | 3/2002 | Miyazaki et al. | |
| 2002/0032583 | A1* | 3/2002 | Joao | 705/2 |
| 2003/0048935 | A1* | 3/2003 | Keren | 382/130 |
| 2003/0053670 | A1* | 3/2003 | Hauper et al. | 382/130 |
| 2003/0099330 | A1* | 5/2003 | Mery et al. | 378/210 |
| 2003/0195414 | A1* | 10/2003 | Chang | 600/413 |
| 2003/0206646 | A1* | 11/2003 | Brackett | 382/128 |
| 2004/0184583 | A1* | 9/2004 | Nagamine et al. | 378/209 |
| 2004/0249806 | A1* | 12/2004 | Kanada | 707/3 |
| 2005/0018895 | A1* | 1/2005 | Kawano | 382/132 |
| 2005/0111757 | A1* | 5/2005 | Brackett et al. | 382/128 |
| 2005/0113680 | A1* | 5/2005 | Ikeda et al. | 600/425 |
| 2005/0197559 | A1* | 9/2005 | Boese et al. | 600/407 |
| 2005/0207538 | A1* | 9/2005 | Mollus et al. | 378/132 |
| 2006/0056680 | A1* | 3/2006 | Stutsman et al. | 382/154 |
| 2006/0083442 | A1* | 4/2006 | Loukipoudis et al. | 382/305 |
| 2007/0058845 | A1* | 3/2007 | Diakides et al. | 382/128 |
| 2007/0118550 | A1* | 5/2007 | Yang et al. | 707/102 |
| 2007/0238963 | A1* | 10/2007 | Kaminaga et al. | 600/407 |
| 2008/0019479 | A1* | 1/2008 | Bernhardt et al. | 378/62 |
| 2008/0071825 | A1* | 3/2008 | Guo | 707/103 R |
| 2008/0123928 | A1* | 5/2008 | Harer et al. | 382/131 |
| 2008/0240360 | A1* | 10/2008 | Jabri | 378/163 |
| 2009/0069668 | A1* | 3/2009 | Stemmer | 600/413 |
| 2009/0297004 | A1* | 12/2009 | Baumgart | 382/130 |
| 2009/0309874 | A1* | 12/2009 | Salganicoff et al. | 345/419 |

OTHER PUBLICATIONS

Waechter et al. "Model Based Blood Flow Quantification from Rotational Angiography" Medical Image Analysis 12 (Feb. 1, 2008) pp. 586-602.*

Urban Malsch, Hartmut Dickhaus, Helmut Kücherer, "Quantitative Analyse von Koronarangiographischen Bildfolgen zur Bestimmung der Myokardperfusion", erschienen in Bildverarbeitung für die Medizin 2003—Algorithmen—Systeme—Anwendungen, Mar. 11, 2003, pp. 81-85, Proceedings des Workshops vom 9, Springer-Verlag.

George Wolberg, "Digital Image Warping", IEEE Computer Society Press Monograph, Jul. 27, 1990, pp. iv-xvi, 187-260, $1^{st}$ edition, Chapter 7, Los Alamitos, California.

* cited by examiner

OPERATING METHOD FOR AN IMAGE-GENERATING MEDICAL ENGINEERING ASSEMBLY AND ARTICLES ASSOCIATED HEREWITH

CROSS REFERENCE TO RELATED APPLICATIONS

This application claims priority of German application No. 10 2005 036 564.7 filed Aug. 3, 2005, which is incorporated by reference herein in its entirety.

FIELD OF THE INVENTION

The present invention relates to an operating method for an image-generating medical engineering assembly comprising a controller and a recording arrangement.

The present invention also relates to a storage medium comprising a computer program stored on the storage medium for carrying out an operating method of this type, a computer comprising a storage medium of this type and an image-generating medical engineering assembly which comprises a recording arrangement and a computer, wherein a computer program is stored in the computer and when it is called up the image-generating medical engineering assembly can be operated according to an operating method of this type. These articles are also generally known.

BACKGROUND OF THE INVENTION

The above-mentioned operating method and the associated devices are used inter alia to capture angiographic photographs (=two-dimensional images) of coronary vessels in a human heart and to then determine the number, length, diameter, etc. of the coronary vessels. Evaluation of the images for measuring the blood flow rate is also known.

A further application of the above-mentioned operating method and the associated devices consists in capturing a sequence of images of the beating heart (or, more generally, an iteratively moving object being examined) over a relatively long time. The sequence of images is captured in this case in response to a user's corresponding start input. Capturing instants of the images and a phase signal (in the case of a beating heart an ECG signal for example) are captured at the same time as the images. The sequence of images, capturing instants and the phase signal are then archived for subsequent evaluations.

With the aid of such sequences what is referred to as the myocardial blush may for example be captured, on the basis of which statements about the blood supply to the heart may be made.

Assessing the blood circulation of the myocardium is associated with difficulties however as it is ultimately a matter of the blood circulation in the tiny capillary vessels which have diameters of only a few micrometers and in which the exchange of oxygen takes place. The angiographically observable cardiac vessels have a diameter of scarcely one millimeter or more, however. A conclusion about the blood circulation of the capillary vessels from the blood circulation of the angiographically observable cardiac vessels is not automatically correct or admissible, however.

The dynamics of the blood flow in the capillary vessels can in principle be detected in the angiographic images by the general (i.e. not localized to individual vessels) contrast enhancement. Owing to problems in application and interpretation this enhancement in the contrast is not generally used, however. In the prior art one therefore often still manages by making conclusions about the blood circulation of the capillary vessels from the blood circulation of the larger coronary vessels.

In order to render the blood flow dynamics in large vessels and the capillary vessels measurable and therefore comparable, various gradation systems are used which divide the continuum of the relationships into discrete classes. Various classifications of this type describe the macroscopic blood circulation and others the capillary blood circulation. The most used classifications have been developed by the scientific organization "Thrombolysis in Myocardial Infarction (TIMI)". These classifications are considered the standard but are complex and merely time-consuming to use. The TIMI classifications are frequently used in multi-centric studies in which the particular focus is on reproducible and comparable results. However, these classifications are not generally applied in routine clinical work. In addition, owing to the individual blush evaluations very different results are produced (in particular with different users).

SUMMARY OF THE INVENTION

The object of the present invention consists in eliminating the restraints in the application of the TIMI classification or a different classification.

The object is achieved in the case of an operating method of the type mentioned at the outset in that:
the controller receives a selection of an image evaluation method from a user and subsequently automatically adjusts selection-specific, positioning-independent operating parameters of the recording arrangement and/or provides the user with instructions for adjusting the positioning-independent operating parameters,
in response to a user's start input the controller captures a sequence of successive two-dimensional images of an iteratively moving object being examined and the capturing instants thereof as well as a phase signal of the object being examined and archives the sequence of images, capturing instants and the phase signal.

For as a result of this it is ensured that the operating parameters of the image-generating medical engineering assembly can always be adjusted so as to be the same, whereby reproducibility as well as comparability of the captured sequences of images is achieved.

Before the start input, the controller preferably also receives from the user a selection for a region of the object being examined and subsequently automatically positions the recording arrangement in a selection-specific manner and/or provides the user with selection-specific instructions for positioning the recording arrangement as this increases the reproducibility and comparability of the sequences even more.

Before archiving, the images to be archived are preferably corrected by detector-specific corrections as it is only then that the archived images are really significant. Before archiving, the images to be archived are preferably not processed further beyond the detector-specific corrections.

The number and type of positioning-independent parameters is very varied. If the recording arrangement comprises an X-ray source and an X-ray detector the positioning-independent operating parameters can for example include at least one of the variables: operating voltage of the X-ray source, operating current of the X-ray source, dimension of an edge enhancement in the captured images, k-factor, γ parameter, image rate and quantity of contrast medium. In particular the positioning-independent operating parameters may also include a plurality of the above-mentioned variables, optionally even all of the above-mentioned variables.

Before the start input, the controller preferably captures an image of the object being examined and outputs this image to the user by way of a display unit as before the start input a visual inspection by the user is possible. Obviously this image captured before the start input is not archived. It may optionally be processed beyond the detector-specific corrections.

The controller preferably outputs a visual and/or acoustic first signal to the object being examined on the basis of the start input because it is then possible for the object being examined to react accordingly. If for example approximately one second before the start a request is output to the object being examined to hold his breath, the object being examined can hold his breath. If before the start of capturing of a sequence of images a further communication is alternatively or additionally output to the object being examined, the object being examined can establish in good time in advance when he should breathe in and then hold his breath.

If the controller supplies trigger pulses to the object being examined, an almost periodic movement of the object for examination can optionally be forced. This is particularly advantageous if the iterations of the object being examined are subject to strong variations without trigger pulses.

The controller preferably controls capturing of the images in such a way that a plurality of groups of images is captured and within each group of images each image is captured at a capturing instant specific to the respective image relative to a preceding instant (reference instant) at which the object being examined assumed a predetermined reference phase position. It is therefore preferred to relate capturing of images with the reference phase position of the object being examined. Sequences of images may consequently be captured, in particular with periodic movement of the object, in which image-group-spanning images with practically the same phase position of the object being examined exist.

In the individual case it is possible for the number of images per group of images to be one. As a rule the number of images per group of images is greater than one, however.

In the latter case it is also possible for capturing instants within each group of images to follow each other at a constant time offset or an inconstant time offset. The earliest capturing instant can alternatively be the reference instant or comes after the reference instant. If the time offset between successive images is constant and the earliest capturing instant is after the reference instant, a time offset between the earliest capturing instant and the reference instant can in particular correspond to the constant time offset.

If on the basis of the start signal the controller automatically injects a contrast medium into the object being examined at a predetermined injection instant or outputs an order to inject the contrast medium to the user, the reproducibility and comparability of the captured sequence of images may be increased even more.

The controller continuously checks whether a termination condition is met. It ceases capturing images as soon as the termination condition is met. The termination condition can be a time lapse, the attainment of a specific number of captured images, the attainment of a specific number of iterations of the object being examined or a user input.

Once capturing of the images has finished, the controller preferably outputs an optical and/or acoustic second signal to the object being examined because, as a result, the object being examined can for example be informed that he may breathe and move again.

In addition to archiving, the captured images can preferably be output directly to the user by way of a display unit. In the process it is possible, before outputting to the user, for the captured images to be corrected by detector-specific corrections and be processed beyond this. A continuous visual inspection by the user is also possible on the basis of outputting of the captured images to the user even during capturing of the sequence of images.

The controller preferably keeps the positioning-independent operating parameters (optionally also the positioning-dependent operating parameters) as constant as possible during capturing of the images. This increases the reproducibility and comparability of the captured images even more. If operating parameters cannot be kept constant then this is at least counteracted as far as possible.

It is possible to completely separate capturing and archiving of the images on the one hand and evaluation of the captured and archived images on the other. However, coupling is also possible. If capturing and archiving on the one hand and evaluation on the other hand are coupled with each other, the controller provides the archived sequence of images, the corresponding capturing instants and the corresponding phase signal of an evaluation device. The user selects at least one of the images as a reference image, whereupon, on the basis of capturing instants and the phase signal, the evaluation device determines further images of the captured sequence as evaluation images automatically or on the basis of corresponding user inputs. On the basis of the reference image and the evaluation images the evaluation device finally automatically draws up a report, allocates it to the captured sequence and archives it. The evaluation device can be identical to the controller in this case. It can, however, also be a device that is different to the controller.

The following approach is preferred for determining the reference image:

the evaluation device automatically selects an image which was captured in the first or last iteration of the object being examined,     the evaluation device determines the phase position of the phase signal on the basis of the capturing instant of the selected image and of the phase signal,     the evaluation device outputs the selected image and the determined phase position to the user by way of a display unit and then waits for a user input.

As a function of the user input, the evaluation device implements one of the following measures: it selects the image captured immediately before the instantaneously selected image or the image captured immediately after the instantaneously selected image, determines the phase position thereof, outputs the now selected image and its phase position to the user by way of the display unit and again waits for the user input.

Or it designates the instantaneously selected image the reference image.

As a result of the above-described approach determination of the reference image is interactive and particularly simple. However it is also possible for the evaluation device to receive a phase position from the user and on the basis of capturing instants and the phase signal designates one of the images, which was captured in the first or last iteration of the object being examined, the reference image.

The evaluation device preferably subtracts the reference image from the evaluation images and thus determines differential images because, as a result, it is possible for the evaluation device to draw up the report on the basis of the differential images. This approach is preferred as the differential images are particularly significant.

If, before the subtraction, the evaluation device carries out an elastic image displacement of the evaluation images, on the basis of which a correlation of the evaluation images with the reference image is maximized, the significance of the differential images may be increased even more. Determination of the elastic image displacements is known per se in this case. By way of example reference is made to the scientific paper "Digital Image Warping" by George Wollberg that appeared in IEEE Computer Society Press Monograph, Wiley-IEEE Computer Society Pr; 1$^{st}$ edition (Jul. 27, 1990), ISBN 0818689447, pages 187 to 260. Alternatively reference may be made to the scientific paper "Quantitative Analyse von Koronarangiographischen Bildfolgen zur Bestimmung der Moyokardperfusion" (Quantitative analysis of coronary angiographical image sequences for the determination of myocardial perfusion) by Urban Malsch et al that appeared in "Bildverarbeitung für die Medizin 2003—Algorithmen—Systeme—Anwendungen" (Image processing for medicine 2003—Algorithms—Systems—Applications) published by Springer, pages 81 to 85.

The evaluation device preferably draws up the report in DICOM format as DICOM format is widely used.

It is particularly advantageous if the evaluation device compares a portion of the evaluation images with the corresponding portion of the reference image, on the basis of the comparison determines a transformation of the pixel values valid for all pixels of the respective evaluation image, so the average value of the pixels of the portion of the transformed evaluation image and the average value of the pixels of the portion of the reference image have a predetermined functional relationship, and transforms the pixels of the respective evaluation image in accordance with this transformation because, as a result, images that can be compared with each other can be generated even if the positioning-independent operating parameters cannot be kept constant. The transformation can alternatively be linear or non-linear. The functional relationship can for example lie in the fact that the difference or quotient of the average values have a predetermined relationship with each other. Transformation can in particular be carried out here such that the difference tends to zero or a minimum, or the quotient tends to one.

It is possible for the portion to be the same for all evaluation images. Alternatively it can be stipulated to the evaluation device by the user or be automatically determined by the evaluation device.

If the evaluation device automatically determines the portion it preferably displaces an evaluation core within a displacement region of the evaluation images or the reference image, determines a variational value characteristic of the variation in the pixels of the evaluation core at each position of the evaluation core, and as a portion designates the evaluation core at the position at which the variational value is minimal. The difference between maximum and minimum average values, the variance, the dispersion, etc. may for example be used as the variational value.

The displacement region can alternatively be automatically determined by the evaluation device or be stipulated to the evaluation device by the user. The displacement region can optionally depend on the selected region of the object being examined. The same applies to the evaluation core.

If the evaluation device outputs the portion, together with the reference image, one of the evaluation images or a differential image determined on the basis of the difference of one of the evaluation images and the reference image, to the user by way of a display unit, a visual inspection by the user is possible. If the differential image is determined in the process, this preferably again takes place by means of an elastic image displacement of the evaluation image used, on the basis of which a correlation of the evaluation image with the reference image is maximized.

The evaluation device preferably draws up the report solely on the basis of the pixel values of at least one inherently cohesive two-dimensional evaluation region of the reference image and the evaluation images as the report is then even more significant. The evaluation region can alternatively be automatically determined by the evaluation device or be stipulated to the evaluation device by the user.

In the case of stipulation by the user it is possible in particular for the evaluation device to suggest a provisional evaluation region to the user and for the user to approve or reject the provisional evaluation region. It is optionally also possible for the user to have the possibility of changing the provisional evaluation region before approval.

As a rule the evaluation region is stipulated once for all images. However it is also possible for the evaluation region to be stipulated to the evaluation device individually for each evaluation image. In this case the evaluation device preferably compares the evaluation regions with each other and outputs an alarm to the user if the evaluation regions do not correspond with each other.

If the object being examined contains a vessel system the evaluation device preferably does not take the regions of the reference image and the evaluation images which correspond to the vessel system into account when drawing up the report as the report is then particularly significant for the myocardial blush. Determining the vessel system is generally known as partitioning. It does not need to be described in more detail therefore.

The evaluation device preferably determines a change over time in the object being examined on the basis of the evaluation images and reference image and by way of a display unit outputs a display characteristic of the change over time in the object being examined to the user. For example the output characteristic display can be a color-coded representation of one of the evaluation images or the reference image, wherein the color is a function of the duration and/or extent of the change over time in the object being examined at the respective location. It is of course also possible to display a matrix, a table or a different representation with corresponding values of the intensity of the myocardial blush as a function of time.

BRIEF DESCRIPTION OF THE DRAWINGS

Further advantages and details can be gathered from the description of an embodiment hereinafter in conjunction with the drawings, in which in a basic illustration.

DETAILED DESCRIPTION OF THE INVENTION

Figure 1:
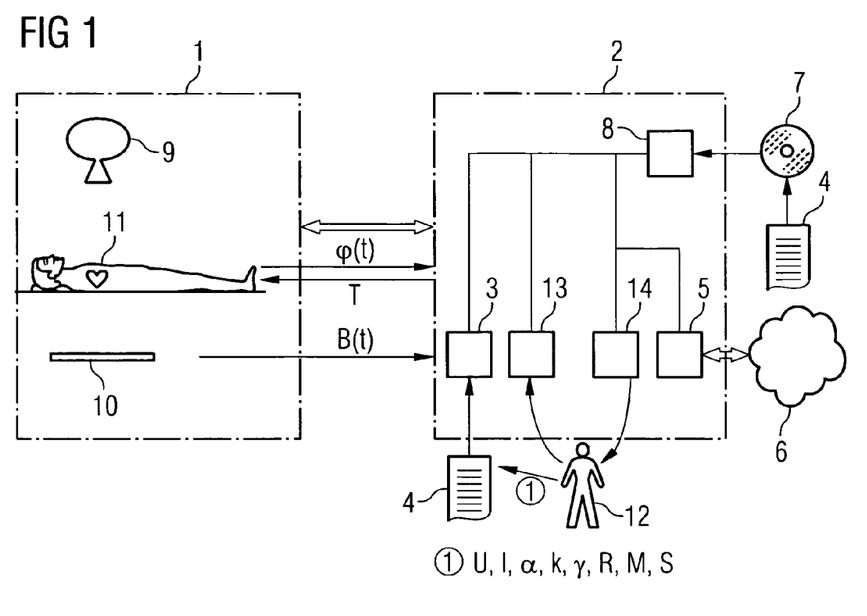
FIG. 1 shows a basic construction of an image-generating medical engineering assembly.

According to FIG. 1 an image-generating medical engineering assembly comprises a recording arrangement 1 and a computer 2. The recording arrangement 1 is controlled by the computer 2. The computer 2 therefore corresponds to a controller for the recording arrangement 1.

The computer 2 comprises a storage medium 3 in the form of a mass storage device, for example in the form of a hard drive. A computer program 4 is stored in the mass storage device 3 and when it is called up the image-generating medical engineering assembly is operated according to an operating method described in more detail hereinafter.

The computer program 4 can have been supplied to the computer 2 in various ways. For example it is possible to supply the computer program 4 to the computer 2 via an interface 5 to a computer network 6. It is also possible to store the computer program 4 on a mobile storage medium 7, i.e. a removable medium, solely in machine-readable form, to couple the removable medium 7 via a suitable interface 8 to the computer 2 and read the computer program 4 out from the removable medium 7 and store it in the mass storage device 3.

According to the embodiment the recording arrangement 1 is constructed as an X-ray assembly. It therefore comprises an X-ray source 9 and an X-ray detector 10, wherein two-dimensional X-ray images B of an object being examined 11 (often a human being) can be captured by means of the X-ray detector 10. The present invention will therefore be illustrated hereinafter in connection with a recording device 1 constructed as an X-ray arrangement and a human being as the object being examined 11. This embodiment should not be regarded as being limiting, however. In so far as the description hereinafter of the operating method according to the invention is based on an X-ray arrangement and a human being it is merely exemplary therefore.

Figure 2:
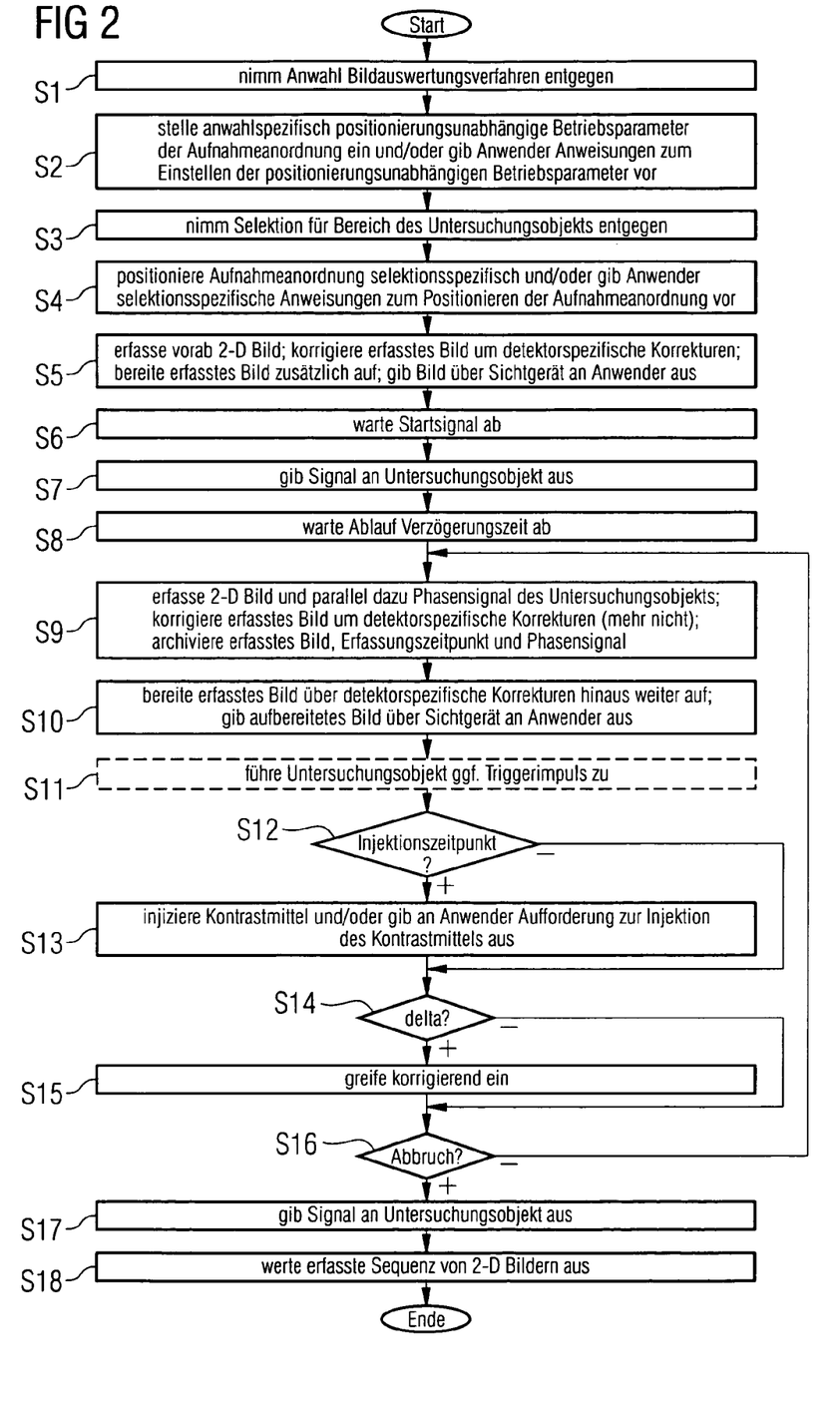
FIG. 2 shows a flow diagram.

According to FIG. 2 in a step S1 the computer 2 firstly receives from a user 12 and via a suitable input device 13 a choice of operating mode. The selected operating mode can for example be a single image mode, a manual mode, swiveling of the recording arrangement 1 to capture images for a three-dimensional reconstruction of the object being examined 11, etc. A corresponding image evaluation method is associated with each of these operating modes. The choice of operating mode therefore simultaneously corresponds to the choice of corresponding image evaluation method.

It will hereinafter be assumed that the user 12 has selected an operating mode in which capturing of a sequence of images B is to take place, which images are to subsequently be used for evaluating what is referred to as myocardial blush. In the specific case the object being examined 11 is therefore not only a human being in general, but the heart thereof. The object being examined 11 is thus an iteratively moving object as the heart obviously beats. For this reason the object being examined 11 also contains a vessel system, namely the coronary vessel system.

As a function of the choice of image evaluation method, i.e. selection-specifically, in a step S2 the computer 2 now adjusts positioning-independent operating parameters U, I, $\alpha$, k, $\gamma$, R, M of the recording arrangement 1. Alternatively it would also be possible to provide the user 12 with corresponding instructions to adjust the positioning-independent operating parameters U, I, $\alpha$, k, $\gamma$, R, M. For example the computer 2 of the recording arrangement 1 can stipulate an operating voltage U of the X-ray source 9, an operating current I of the X-ray source 9, a dimension $\alpha$ of an edge enhancement in the captured images B, a k-factor k, a $\gamma$ parameter $\gamma$, an image rate R and a quantity of contrast medium M. The adjusted or stipulated operating parameters U, I, $\alpha$, k, $\gamma$, R and/or M can alternatively be strictly predetermined, i.e. be set by the manufacturer of the medical engineering assembly. It is also possible, however, that the user 12 has determined them at another opportunity. The crucial factor is that the values are predetermined.

It is possible to capture various regions of the object being examined 11. In a step S3 the computer 2 therefore preferably receives from the user 12 a choice or selection for a region of the object being examined 11. Depending on the selected region other positionings of the recording arrangement 1 relative to the object being examined 11 are then optimal. In a step S4 the computer 2 therefore positions the recording arrangement 1 according to the selection of step S3 or provides the user 12 with corresponding selection-specific instructions for positioning the recording arrangement 1. It is also crucial here for the positionings to be predetermined. By contrast, it is of secondary importance whether the positionings are determined by the manufacturer of the image-generating medical engineering assembly or by the user 12.

The computer 2 then captures in a step S5 a two-dimensional image B by means of an X-ray detector 10. It corrects this image B—likewise within the framework of step S5—by detector-specific corrections. It also additionally processes the captured imaged and outputs it by way of a display unit 14 to the user. The user 12 thus has the possibility of visually affirming that the adjustments and operating parameters (positioning-dependent and positioning-independent) are valid.

In a step S6 the computer 2 then waits for a start signal S from the user 12.

When the user 12 provides the start signal S, in a step S7 the computer 2 firstly outputs an optical and/or acoustic signal to the object being examined 11. The significance of the outputting of the first signal consists in informing the object being examined that capturing of a sequence of images B will presently start, namely after a delay time has elapsed. The object being examined therefore still has time to breathe in for example and hold his breath, etc. The computer 2 waits for the delay time to elapse in a step S8.

After the delay time has elapsed, the computer 2 captures in a step S9 a two-dimensional image B and simultaneously therewith a phase signal $\phi$ of the object being examined 11. The computer 2 corrects this image B within the framework of step S9 by detector-specific corrections but does not process it any further. The computer 2 archives the corrected captured image B. The capturing instant t of the image and the phase signal $\phi$ are archived together with the image.

In a step S10 the computer 2 also processes the captured image B beyond the detector-specific corrections and outputs the processed image B by way of the display unit 14 directly to the user 12. Permanent visual inspection by the user 12 is consequently possible.

According to FIG. 2 it is also optionally possible in a step S11 to supply the object being examined with trigger pulses T. This may possibly be expedient if the human heart beats very irregularly or only weakly for example. As a rule it is not necessary to supply trigger pulses T, however. Step S11 is therefore merely optional and for this reason it is only shown in broken lines in FIG. 2.

In a step S12 the computer 2 also checks whether—calculated from the start signal S—an injection instant has been reached at which a contrast medium is to be injected into the object being examined 11. When this injection instant is reached the computer 2 injects the contrast medium in a step S13 or outputs to the user 12 a corresponding order to inject the contrast medium. Otherwise the method proceeds directly to step S14.

In step S14 the computer checks whether the positioning-independent operating parameters U, I, $\alpha$, k, $\gamma$, R, M have changed during capturing of the images B. If so, the computer 2 intervenes in a step S15 in a correcting manner, so the operating parameters U, I, $\alpha$, k, $\gamma$, R, M are kept as constant as possible. Otherwise the method proceeds directly to step S16.

In step 16 the computer 2 checks whether a termination condition is met. The termination condition can be in this case for example a time lapse, the attainment of a specific number of captured images B, the attainment of a specific number of iterations of the object being examined 11 or a user 12 input.

If the termination criterion is not met the computer 2 returns to step S9 where it captures the next image. If the termination criterion is met on the other hand, the computer 2 ceases capturing of images B and proceeds to step S17. In this step S17 the computer 2 outputs a visual and/or acoustic second signal to the object being examined 11. The object being examined 11 therefore knows that he is allowed to breathe again and/or move for example.

The manner of capturing the individual two-dimensional images B can be configured in different ways. This will be described in more detail hereinafter in connection with FIGS. 3 to 8.

Figure 3:
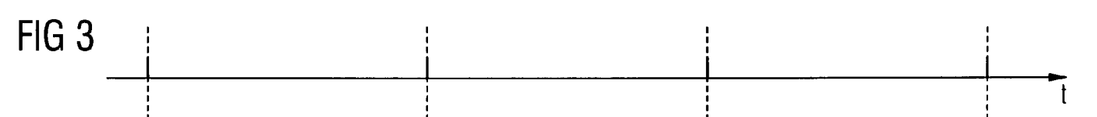
FIGS. 3 to 8 show time-dependency graphs.

FIG. 3 firstly shows a plurality of instants at which the object being examined 11 assumes a respective reference phase position. The reference phase position can for example correspond to the R-wave of an ECG.

Figure 4:
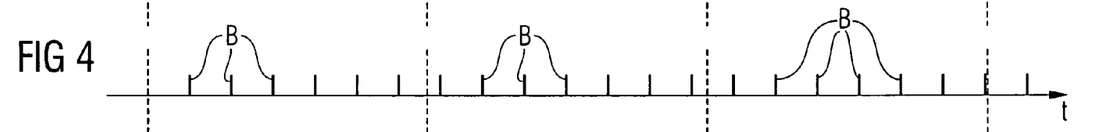

In the simplest case the individual two-dimensional images B are captured independently of the reference instants. This case is illustrated in FIG. 4.

However, it is also possible for the computer 2 to control capturing of the images B in such a way that a plurality of groups of images B is captured. Within each group of images B each image B is then captured at a capturing instant specific to the respective image B relative to a preceding instant (reference instant) at which the object being examined 11 has assumed the reference phase position. Case manipulations of this type are illustrated in FIGS. 5 to 8.

Figure 5:
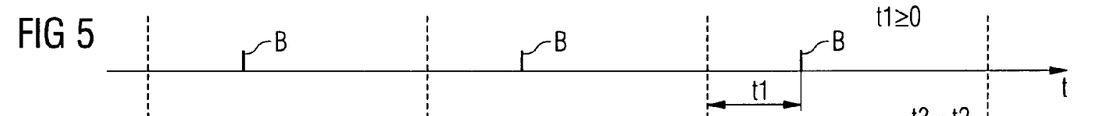

According to FIG. 5 the number of images B per group of images B is one. A time offset t1 between the respective reference instants and capturing instants of the images B can also be zero or greater than zero in this case.

As a rule the number of images B per group of images is greater than one, however. These case manipulations are illustrated in FIGS. 6 to 8.

Figure 6:
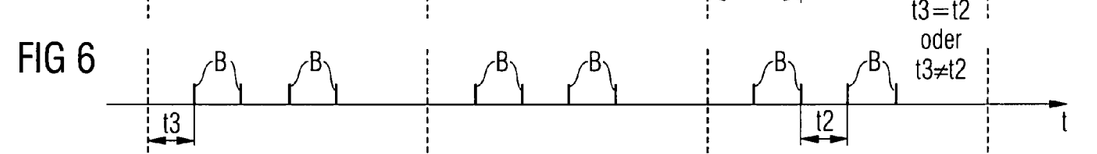
Figure 7:
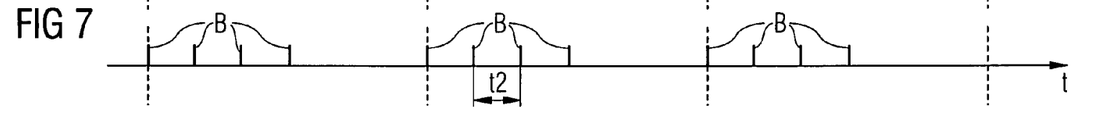

According to FIGS. 6 and 7 capturing instants within each group of images B follow each other at a constant time offset t2. The difference between FIGS. 6 and 7 lies in the fact that in FIG. 6 the earliest capturing instant is at a time offset t3 after the reference instant, while in FIG. 7 the earliest capturing instant is the reference instant itself. According to FIG. 6 there is thus a time offset t3 between the reference instant and the earliest capturing instant. This time offset t3 may also be the same as the time offset t2 or different from the time offset t2.

Figure 8:
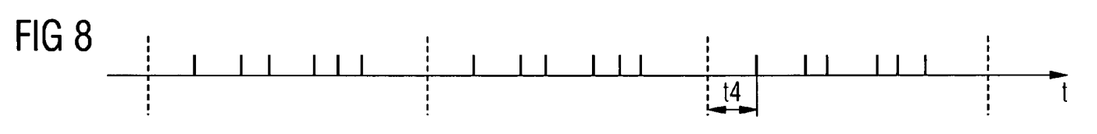

According to FIG. 8 it is possible for capturing instants within each group of images B to not follow each other at a constant time offset. This may be gathered from FIG. 8 on the basis of the different spacings of the individual images B from each other. A time offset t4 from the respective reference instant to capturing instant of the first image B of the respective group can alternatively be zero or greater than zero.

The captured and archived images must of course also be evaluated. This takes place in a step S18. It is possible for the computer 2 to execute step S18 itself. In this case it provides itself with the archived sequence of images B, the corresponding capturing instants t and the corresponding phase signal $\phi$. In this case it therefore itself simultaneously constitutes an evaluation device for the captured sequence of images B. However, it is also possible to provide an evaluation device which is different from the computer 2 with the captured sequence of images B, the corresponding capturing instants t and the corresponding phase signal $\phi$. It will be assumed by way of example hereinafter that the computer 2 itself also assumes the function of the evaluation device.

Within the context of evaluation of the captured sequence of images B the user 12 firstly selects one of the images B as a reference image. The computer 2 receives this choice according to FIG. 9 in a step S21. Two preferred approaches are possible for selection of the reference image. These two approaches will be described in more detail hereinafter in connection with FIGS. 10 and 11.

Figure 10:
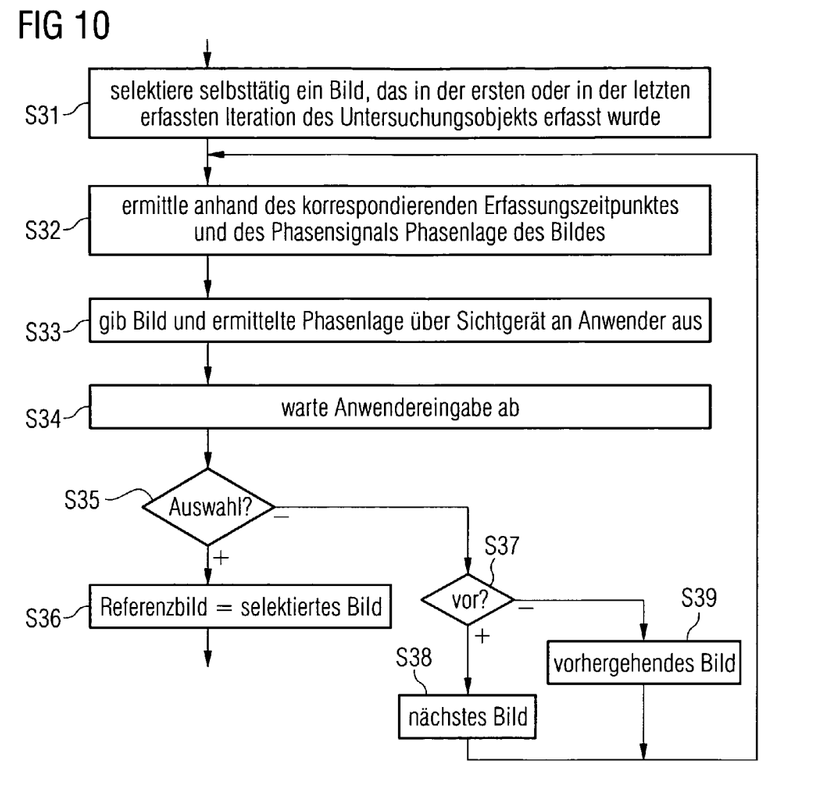

According to FIG. 10 to select the reference image the computer 2 firstly automatically selects in a step S31 an image B which has been captured in the first or last iteration of the object being examined 11. In a step S32 the computer 2 then determines a phase position of the selected image B on the basis of the corresponding capturing instant t and the phase signal $\phi$. The computer outputs the selected image B and the determined phase position to the user 12 by way of the display unit 14 in step S33 and then waits for a user input in a step S34.

In a step S35 the computer 2 checks whether the user input was a selection. If so, in a step S36 the computer 2 designates the instantaneously selected image B the reference image. Otherwise the computer checks in a step S37 whether the user input was a command to page forward. If so, the computer 2 selects in a step S38 the image B captured immediately after the instantaneously selected image B and returns to step S32. Otherwise the computer 2 selects the image B captured immediately before the instantaneously selected image B and likewise returns to step S32.

Figure 11:
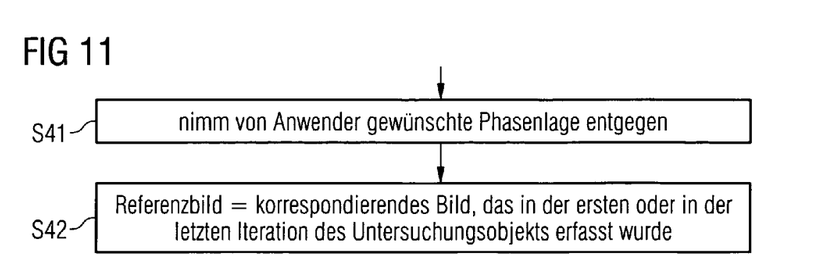

Alternatively, according to FIG. 11 it is also possible for the user 12 to stipulate a desired phase position to the computer 2 in a step S41. In this case, in a step S42 the computer 2 designates, on the basis of capturing instants t and the phase signal $\phi$, one of the images B which was captured in the first or last iteration of the object being examined 11 the reference image in a step S42.

Figure 9:
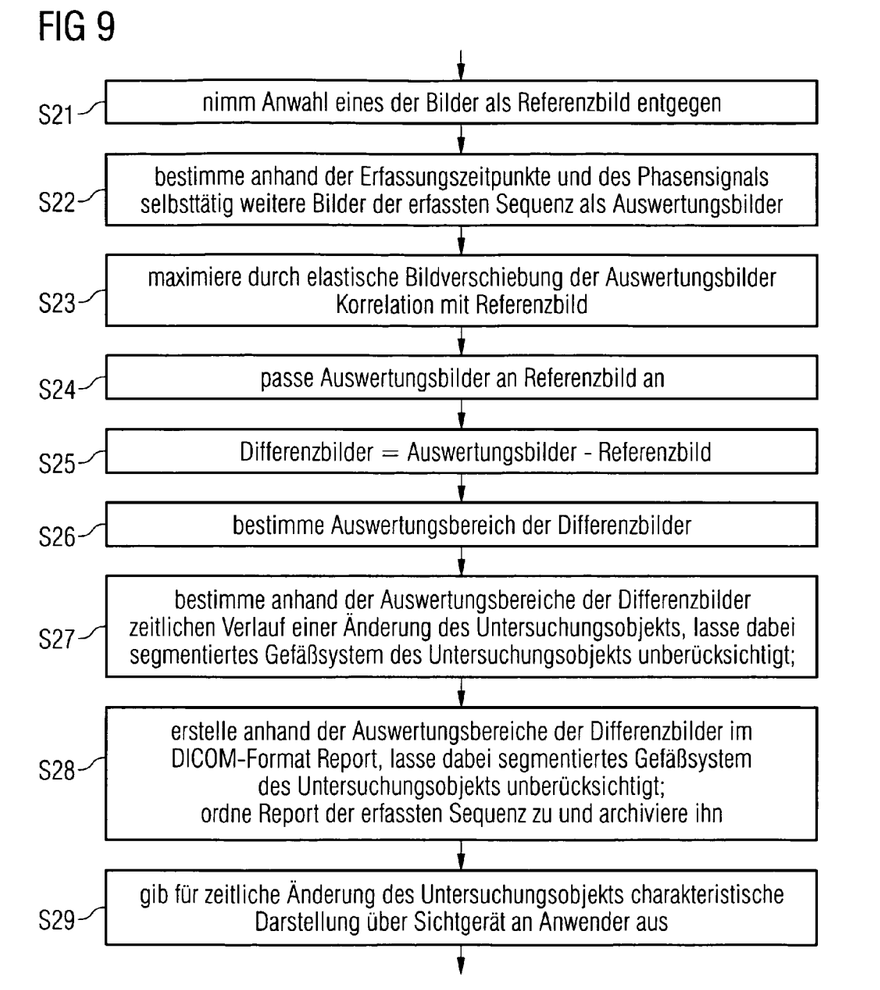
FIGS. 9 to 14 show flow diagrams.

After determining the reference image the computer 2 continues the evaluation of the captured sequence of images B according to FIG. 9 with a step S22. In step S22 the computer 2 automatically designates further images B of the captured sequence evaluation images on the basis of capturing instants t and the phase signal $\phi$. This determination preferably takes place automatically via the computer 2. However interactive determination by appropriate auxiliary user 12 inputs is also possible.

The computer 2 preferably next determines in a step S23 elastic image displacements of the evaluation images and implements these elastic displacements. The elastic displacements are determined in such a way that a correlation with the reference image is maximized for the respectively considered image.

The computer 2 then adapts the evaluation images in a step S24 to the reference image. This step S24 will be described in more detail hereinafter in connection with FIG. 12.

Figure 12:
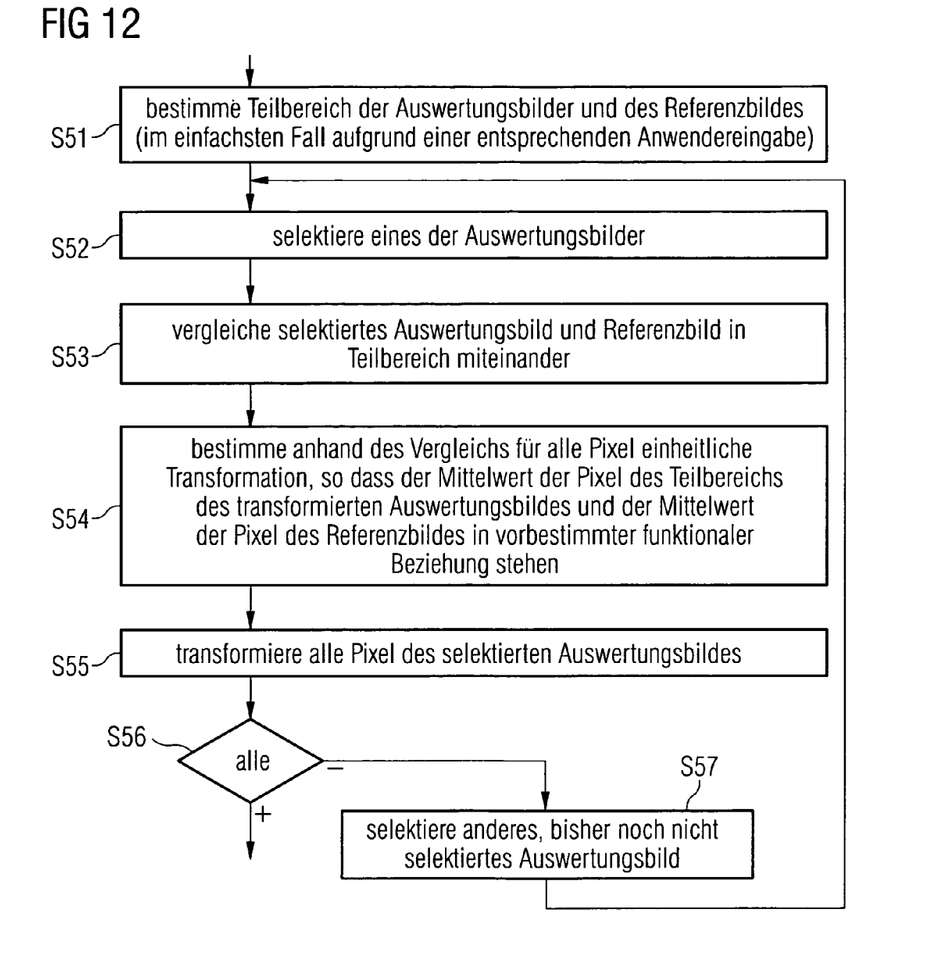

According to FIG. 12 the computer 2 firstly determines in a step S51 a portion of the evaluation images and the reference image. In the simplest case this determination is made on the basis of a corresponding input by the user 12. However it is also possible for the computer 2 to automatically determine the portion. This will be described in more detail later in connection with FIG. 13.

After determining the portions, in a step S52 the computer 2 selects one of the evaluation images. In a step S53 the computer 2 then compares the selected evaluation image and the reference image. The comparison is made in this case only within the mutually corresponding portions. The computer 2 then determines in a step S54 a transformation of the pixel values of the selected evaluation image on the basis of the comparison. The transformation is determined in such a way that the average value of the pixels of the portion of the transformed evaluation image on the one hand and the average value of the pixels of the reference image on the other hand have a functional relationship with each other. The functional relationship can consist in particular in that the average value of the pixels of the portion of the transformed evaluation image is identical to the average value of the pixels of the portion of the reference image. The transformation may alternatively be linear or non-linear.

In a step S55 the computer 2 then transforms all pixels of the selected evaluation image, i.e. both inside and outside the portion, in accordance with the transformation determined in step S54.

In a step S56 the computer 2 checks whether it has already carried out the steps S52 to S55 for all evaluation images. If this is not yet the case it firstly proceeds to a step S57 in which it selects a different evaluation image and then returns to step S52. Otherwise adaptation of the evaluation images according to step S24 of FIG. 9 is complete.

As already mentioned in connection with FIG. 12, determination of the portion by a corresponding user input is the simplest case. Determination of the portion by the computer 2 will now be described in more detail hereinafter in connection with FIG. 13. Regardless of the question of whether determination of the portion takes place by way of a corresponding user input or automatically by the computer 2, the portion is preferably the same for all evaluation images, however.

Figure 13:
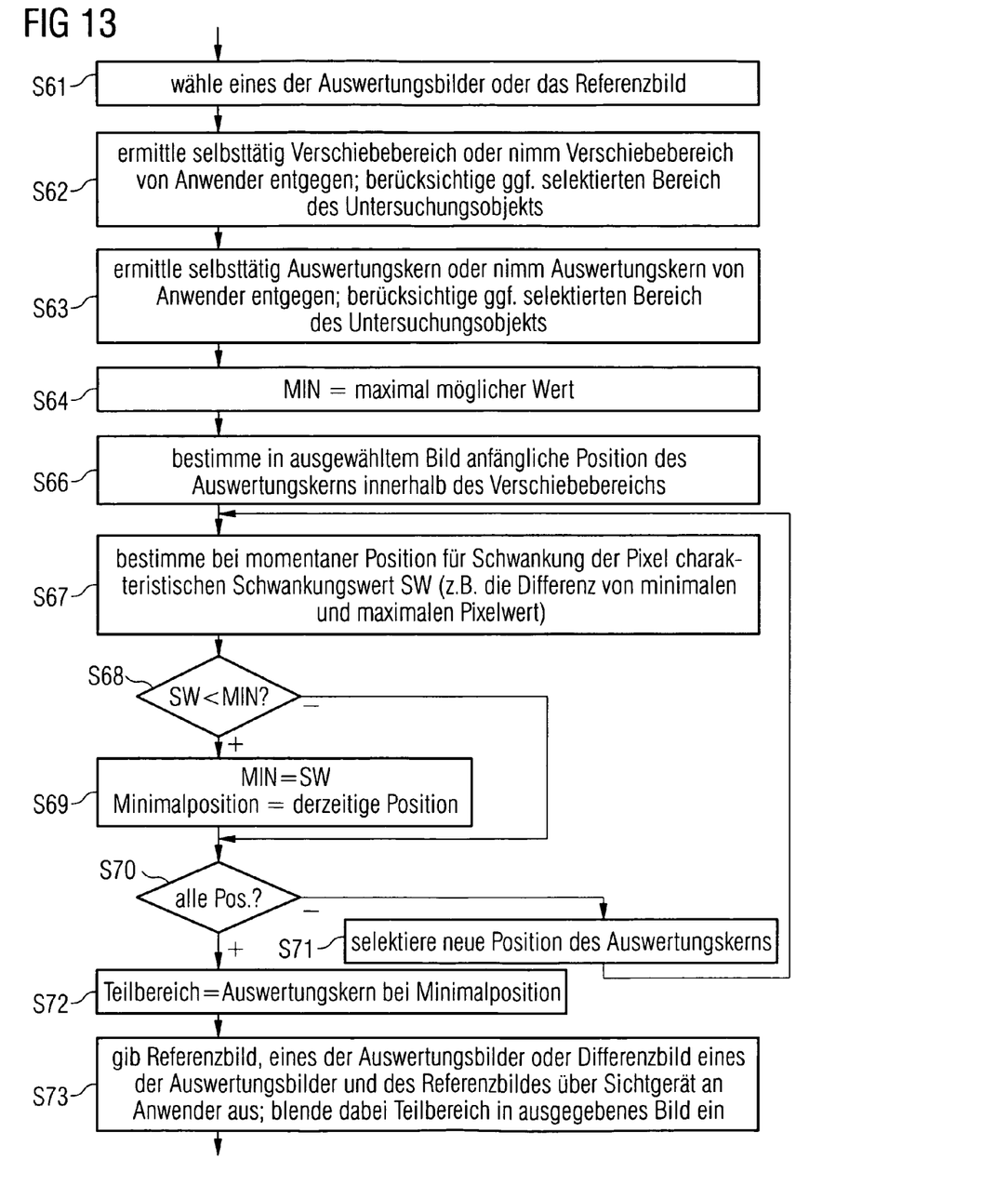

If the computer 2 automatically determines the portion, according to FIG. 13 the computer 2 firstly selects in a step S61 one of the evaluation images or the reference image. In the selected image the computer 2 then determines in a step S62 a displacement region or receives a displacement region from the user 12. If required the computer 2 in the process takes into account the selected region of the object being examined 11.

If the computer 2 automatically determines the displacement region this can for example take place in that it automatically selects a quadrant or part of a quadrant which corresponds to the displacement region. If the displacement region is stipulated to the computer 2 by the user 12 it is possible for example for the user 12 to mark a traverse or rectangle in the selected image.

In both cases it is possible to take into account the selected region of the object being examined 11 when determining the displacement region. For example the computer 2 can determine the quadrant or part thereof as a function of the selected region of the object being examined 11. A framework region, within which the displacement region must be located, may also be determined as a function of the selected region of the object being examined 11 in the case of an input by the user 12.

The displacement region is a region in which an evaluation core yet to be established is displaced. Like the displacement region the two-dimensional evaluation core is determined in a step S63. Automatic determination by the computer 2 or a stipulation by the user 12 may also alternatively take place in this case also. The selected region of the object being examined 11 can optionally again also be taken into account here.

Next a variable MIN is set to a maximum possible value in a step S64 for actual determination of the portion. An initial (in principle any desired) position of the evaluation core within the displacement region in the selected image is furthermore determined in a step S66.

In a step S67 the computer 2 determines at the instantaneous position a variational value SW which is characteristic of the variation in the pixels within the evaluation core at the instantaneously determined position of the evaluation core. For example the difference from maximum and minimum pixel values or a random variable, such as dispersion or variance, can be determined.

In a step S68 the computer 2 checks whether the variational value SW is less than the variable MIN. If this is the case the computer 2 sets the variable MIN to the variational value SW in a step S69 and stores the current position as a minimal position. Otherwise the computer proceeds directly to step S70.

In step S70 the computer 2 checks whether it has already executed steps S67 to S69 for all possible positions of the evaluation core within the displacement region. If this is not the case the computer 2 proceeds to a step S71 in which it determines a new, not yet evaluated position of the evaluation core. It then returns to step S67. Otherwise the computer designates in a step S72 the evaluation core at the minimal position the portion. In a step S73 the computer 2 then outputs the reference image, one of the evaluation images or a differential image of one of the evaluation images and the reference image to the user 12 by way of the display unit 14. It then fades the portion into the output image.

Provided it has not already taken place otherwise differential images are formed next according to FIG. 9 in a step S25 by subtracting the reference image from the evaluation images. A section of the differential images is furthermore selected in a step S26. Selection of the section will be described in more detail hereinafter in connection with FIG. 14.

Figure 14:
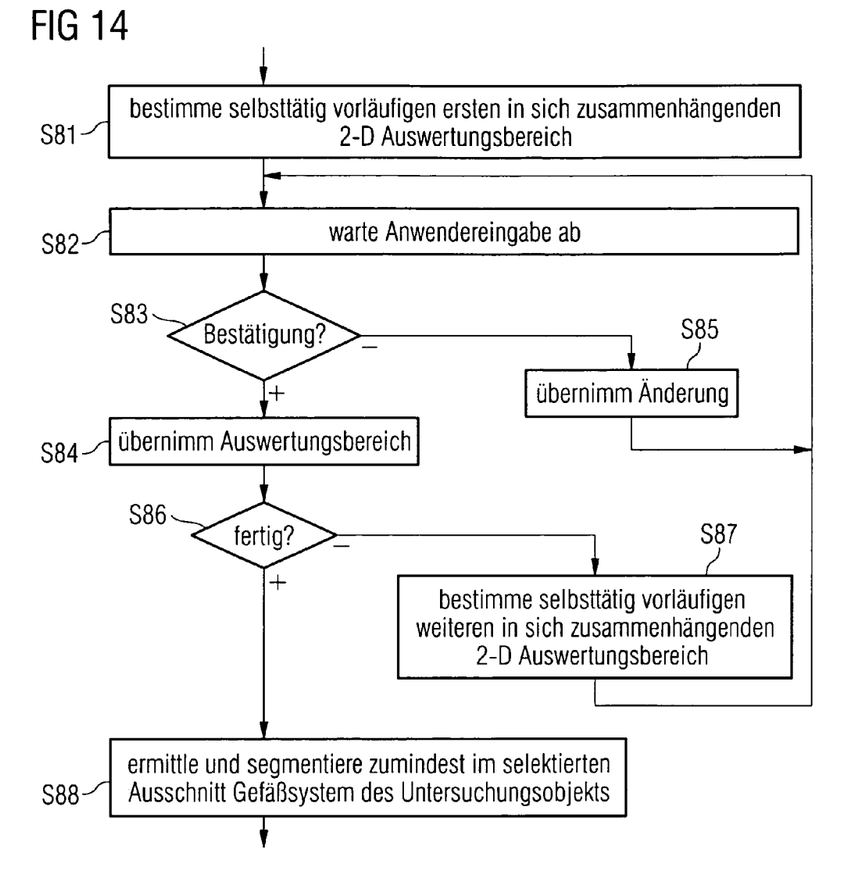

According to FIG. 14 the computer 2 firstly automatically determines in a step S81 a first inherently cohesive two-dimensional evaluation region. However, this evaluation region is only provisional. The computer 2 then waits in a step S82 for a user input.

In a step S83 the computer 2 checks whether the user input was an approval. If so, in a step S84 the computer 2 accepts the self-contained evaluation region as the selected evaluation region. Otherwise in a step S85 the computer 2 accepts a user's 12 modification instruction and returns to step S82.

Obviously the user 12 does not just have the possibility of approving and changing the provisional evaluation region; he may also reject it. This is not shown in FIG. 14 merely for the sake of clarity.

In a step S86 the computer 2 next checks whether determination of the evaluation regions is now completed. If this is not the case the computer 2 automatically determines in a step S87 a further provisional self-contained evaluation region and returns to step S82. Otherwise determination of the evaluation regions is completed.

Steps S82 to S85 are merely optional. They may therefore optionally be omitted. If this is the case, i.e. if steps S82 to S85 are omitted, the computer 2 determines the evaluation regions completely automatically.

After determining the selected section the computer 2 carries out another step S88 according to FIG. 14. In this step S88 the computer 2 partitions the vessels of the object being examined 11 in the evaluation region of the differential images. It then continues with further execution of the operating method according to the invention in a step S27 (see FIG. 9).

As a rule the selected section is determined once for all differential images. However, it is also possible for the user 12 to determine the evaluation region individually for each evaluation image and to stipulate it to the computer 2 accordingly. In this case the computer 2 compares the evaluation regions of the individual evaluation images with each other. It outputs an alarm to the user 12 if the evaluation regions do not correspond with each other.

In step S27 the computer 2 determines a time dependent course of a change in the object being examined 11 on the basis of the selected sections of the differential images. It ignores the vessel system, partitioned in step S88, of the object being examined 11 in this case.

In a subsequent step S28 the computer 2 automatically draws up a report, allocates it to the captured sequence and archives it. The report is drawn up on the basis of the differential images determined in step S25, more precisely: solely on the basis of the pixel values of the differential images in the evaluation region. Owing to partitioning of the vessel system in step S88, the computer 2 does not takes into account the vessel system when drawing up the report.

The format of the report can in principle be selected as desired, but the computer 2 preferably draws up the report in DICOM format.

Figure 15:
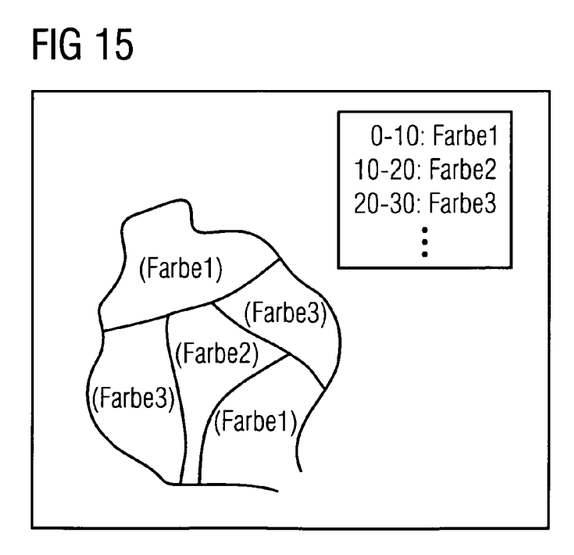
FIG. 15 shows diagrammatically a color-coded image.

Beyond drawing up the report the computer 2 in a step S20 also outputs to the user 12 by way of the display unit 14 a display which is characteristic of the change over time in the object being examined 11. For example it is possible—see FIG. 15—to show a color-coded representation of one of the evaluation images or the reference image or one of the differential images on the display unit 14. In this case the color is a function of the duration and/or extent of the change over time in the object being examined 11. A corresponding color scale may be faded into the image shown.

By means of the operating method according to the invention it is thus possible to capture reproducible sequences of images of the object being examined 11 much more reliably than has previously been possible.

The invention claimed is:

1. An operating method for an image-generating medical engineering assembly having a controller and a recording arrangement, comprising:
   receiving a selection of an image evaluation method from a user by the controller;
   providing the user with an instruction for adjusting a positioning-independent operating parameter of the recording arrangement base on the selection;
   capturing a sequence of successive two-dimensional images of an object being examined and capturing instants of the images as well as a phase signal of the object in response to a start input of the user, the object being an iteratively moving object; and
   archiving the captured sequence of images, the capturing instants and the phase signal,
   wherein the controller comprises an evaluation device with the archived captured sequence of images, the capturing instants and the phase signal,
   wherein the user selects one of the captured sequence of images as a reference image,
   wherein the evaluation device determines a further image of the captured sequence of images as an evaluation image automatically or based on a user input,
   wherein the evaluation device automatically draws up a report allocating to the captured sequence based on the reference image and the evaluation image and archives the report,
   wherein the evaluation device further:
   automatically selects an image which is captured in the first or last iteration of the object as the reference image,
   determines a phase position of the phase signal based on a capturing instant of the selected image,
   outputs the selected image and the determined phase position to the user for a consideration of the reference image,
   determines the reference image by:
      designating the selected image as the reference image if the user selects the selected image as the reference image, or
      selecting a further image captured immediately before or after the selected image, determining a phase position thereof, and outputting the further selected image and the phase position to the user for further consideration of the reference image if the user denies the selected image as the reference image.

2. The operating method as claimed in claim 1, wherein the operating parameter is automatically adjusted.

3. The operating method as claimed in claim 1, wherein before capturing the sequence of images, the controller:
   receives a selection of a region of the object from the user and automatically positions the recording arrangement accordingly or provides the user with an instruction for positioning the recording arrangement,
   captures an image of the object and outputs the image to the user by a display unit.

4. The operating method as claimed in claim 1,
   wherein before archiving, the images to be archived are corrected by a detector-specific correction and are not processed further beyond the correction.

5. The operating method as claimed in claim 1, wherein the recording arrangement comprises an X-ray source and an X-ray detector and the operating parameter of the recording arrangement is selected from the group consisting of: operating voltage of the X-ray source, operating current of the X-ray source, dimension of an edge enhancement in the images, k-factor, γ parameter, image rate, and quantity of contrast medium.

6. The operating method as claimed in claim 1, wherein the controller:
   outputs a first visual or acoustic signal to the object after receiving the start input,
   supplies the object with trigger pulses,
   controls capturing of the sequence of images such that each image is captured at a specific capturing instant relative to a preceding instant as a reference instant at which the object is assumed a predetermined reference phase position, wherein a time offset between the respective reference instants and capturing instants of the images is zero or greater than zero,
   maintains the operating parameter substantially constant during the capturing,
   automatically injects a contrast medium into the object at a predetermined injection instant or outputs an order to inject the contrast medium to the user,
   continuously checks whether a termination condition is met and ceases capturing images when the termination condition is met,
   outputs a second optical or acoustic signal to the object after finishing the capturing of the images.

7. The operating method as claimed in claim 6, wherein the termination condition is selected from the group consisting of: a time lapse, an attainment of a specific number of captured images, an attainment of a specific number of iterations of the object, and a user input.

8. The operating method as claimed in claim 1, wherein the evaluation device receives a phase position from the user and designates one of the images which is captured in the first or last iteration of the object as the reference image based on the capturing instants and the phase signal.

9. The operating method as claimed in claim 1, wherein the evaluation device:
   carries out an elastic image displacement of the evaluation images based on a correlation of the evaluation images with the reference image,
   subtracts the reference image from the evaluation images, determines differential images based on the subtraction, and draws up a report in DICOM format based on the differential images.

10. The operating method as claimed in claim 1, wherein the evaluation device:
   compares a portion of the evaluation image with a corresponding portion of the reference image,
   determines a transformation of a pixel value valid for all pixels of the evaluation image based on the comparison so that an average pixel value of the portion of the transformed evaluation image and an average pixel value of the portion of the reference image have a predetermined functional relationship, and
   transforms the pixels of the evaluation image according to the transformation,
   outputs the portion together with the reference image, the evaluation image or a differential image by subtracting the reference image from the evaluation image to the user.

11. The operating method as claimed in claim 10, wherein the portion is identical for all evaluation images or stipulated by the user or automatically determined by the evaluation device.

12. The operating method as claimed in claim 11, wherein for automatically determining the portion within a displacement region of the evaluation image or the reference image, the evaluation device:
   displaces a two-dimensional evaluation core,
   determines a characteristic value of a variation in the pixels of the evaluation core at each position of the evaluation core, and
   designates the evaluation core at a position which the characteristic value is minimal as the portion.

13. The operating method as claimed in claim 12, wherein the displacement region and the evaluation core are automatically determined by the evaluation device or stipulated by the user or depended on the selected region of the object.

14. The operating method as claimed in claim 1,
   wherein the evaluation device draws up the report solely based on pixel values of at least one inherently cohesive two-dimensional evaluation region of the reference image and the evaluation image which does not include a region of a vessel system of the object,
   wherein the evaluation region is automatically determined by the evaluation device or stipulated by the user or suggested by the evaluation device to the user for an approval.

15. The operating method as claimed in claim 14, wherein the evaluation region is individually stipulated for each evaluation image and an alarm is output to the user if the evaluation region changes with each other.

16. The operating method as claimed in claim 1,
   wherein the evaluation device determines a change of the object over a period of time based on the evaluation image and the reference image, and outputs a display characteristic of the change to the user,
   wherein the characteristic display is a color-coded representation of the evaluation image or the reference image or a differential image, and the color is a function of a duration or an extent of the change.

17. A non-transitory computer readable storage medium encoded with instructions that, when executed on a computer, performs an operating method for an image-generating medical engineering assembly having a recording arrangement and a computer, the method comprising: receiving a selection or an image evaluation method from a user by the controller; providing the user with an instruction for adjusting a positioning-independent operating parameter of the recording arrangement base on the selection; capturing a sequence of successive two-dimensional images of an object being examined and capturing instants of the images as well as a phase signal of the object in response to a start input of the user, the object being an iteratively moving object; and archiving the captured sequence of images, the capturing instants and the phase signal,
   wherein the controller comprises an evaluation device with the archived captured sequence of images, the capturing instants and the phase signal,
   wherein the user selects one of the captured sequence of images as a reference image,
   wherein the evaluation device determines a further image of the captured sequence of images as an evaluation image automatically or based on a user input,
   wherein the evaluation device automatically draws up a report allocating to the captured sequence based on the reference image and the evaluation image and archives the report, wherein the evaluation device further:
   automatically selects an image which is captured in the first or last iteration of the object as the reference image,
   determines a phase position of the phase signal based on a capturing instant of the selected image,
   outputs the selected image and the determined phase position to the user for a consideration of the reference image determines the reference image by:
   designating the selected image as the reference image if the user selects the selected image as the reference image, or
   selecting a further image captured immediately before or after the selected image determining a phase position thereof, and outputting the further selected image and the phase position to the user for further consideration of the reference image if the user denies the selected image as the reference image.

18. An image-generating medical engineering assembly, comprising:
   a recording arrangement; and
   a computer, wherein the computer stores instructions that, when executed on the computer, perform an operating method, comprising:
   receiving a selection of an image evaluation method from a user by the controller;
   providing the user with an instruction for adjusting a positioning-independent operating parameter of the recording arrangement base on the selection;
   capturing a sequence of successive two-dimensional images of an object being examined and capturing instants of the images as well as a phase signal of the object in response to a start input of the user, the object being an iteratively moving object; and
   archiving the captured sequence of images, the capturing instants and the phase signal
   wherein the controller comprises an evaluation device with the archived captured sequence of images, the capturing instants and the phase signal,
   wherein the user selects one of the captured sequence of images as a reference image,
   wherein the evaluation device determines a further image of the captured sequence of images as an evaluation image automatically or based on a user input,
   wherein the evaluation device automatically draws up a report allocating to the captured sequence based on the reference image and the evaluation image and archives the report,
   wherein the evaluation device further:
   automatically selects an image which is captured in the first or last iteration of the object as the reference image,
   determines a phase position of the phase signal based on a capturing instant of the selected image,
   outputs the selected image and the determined phase position to the user for a consideration of the reference image, determines the reference image by:
designating the selected image as the reference image if the user selects the selected image as the reference image, or
selecting a further image captured immediately before or after the selected image, determining a phase position thereof, and outputting the further selected image and the phase position to the user for further consideration of the reference image if the user denies the selected image as the reference image.

* * * * *